United States Patent [19]

Baker et al.

[11] Patent Number: 4,645,743

[45] Date of Patent: Feb. 24, 1987

[54] METHOD AND DEVICE FOR COLLECTING AND TESTING FOR FECAL OCCULT BLOOD

[75] Inventors: Josefina T. Baker, Cupertino, Calif.; Joseph F. Pagano, Paoli, Pa.; Ronald J. Schoengold, San Jose, Calif.

[73] Assignee: SmithKline Diagnostics, Inc., Sunnyvale, Calif.

[21] Appl. No.: 838,856

[22] Filed: Mar. 11, 1986

[51] Int. Cl.$^4$ .............................................. G01N 33/72
[52] U.S. Cl. ...................................... 436/66; 128/638; 128/759; 422/56; 422/58; 422/61; 436/904
[58] Field of Search .................... 422/56, 57, 58, 61; 436/66, 904; 128/638, 749, 759; 435/28

[56] References Cited

U.S. PATENT DOCUMENTS

| | | | |
|---|---|---|---|
| 4,273,741 | 6/1981 | Levine | 422/56 |
| 4,365,970 | 12/1982 | Lawrence | 436/66 |
| 4,559,949 | 12/1985 | Levine | 422/56 |

FOREIGN PATENT DOCUMENTS

| | | | |
|---|---|---|---|
| 0117689 | 5/1984 | European Pat. Off. | 435/28 |
| 0124215 | 7/1984 | European Pat. Off. | 435/28 |
| 7805023 | 11/1978 | Netherlands | 128/749 |
| 2031583 | 4/1980 | United Kingdom | 422/56 |

Primary Examiner—Barry S. Richman
Assistant Examiner—Lori-Ann Cody
Attorney, Agent, or Firm—Joseph A. Marlino; Stuart R. Suter; Alan D. Lourie

[57] ABSTRACT

A method and device for collecting and testing fecal occult blood which permits multiple analyses of a single fecal sample. The device is a combination of a sampler for collecting the fecal matter and a test slide. The fecal sampler comprises a pocket-like wipe pad for obtaining direct anal stool smears. An insert is disposed in the pocket of the wipe pad. The slide has a profiled opening similar to the design of the wipe pad. This opening acts as a receptacle for the pad when the fecal smear is transferred to the guaiac specimen receiving sheet of the slide. When the slide is closed the insert can be removed from the wipe pad. This design permits an analysis to be done on the specimen receiving sheet of the slide together with a second confirmatory test for human hemoglobin on portions of the insert. The fecal material on the insert is physically removed from the guaiac specimen receiving sheet.

8 Claims, 14 Drawing Figures

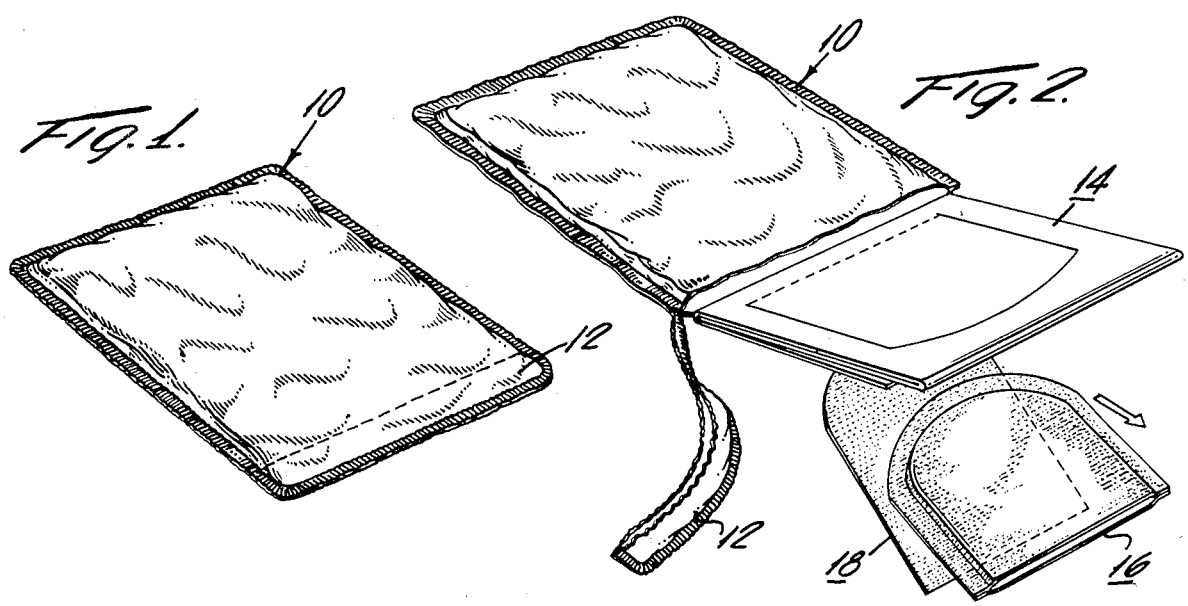
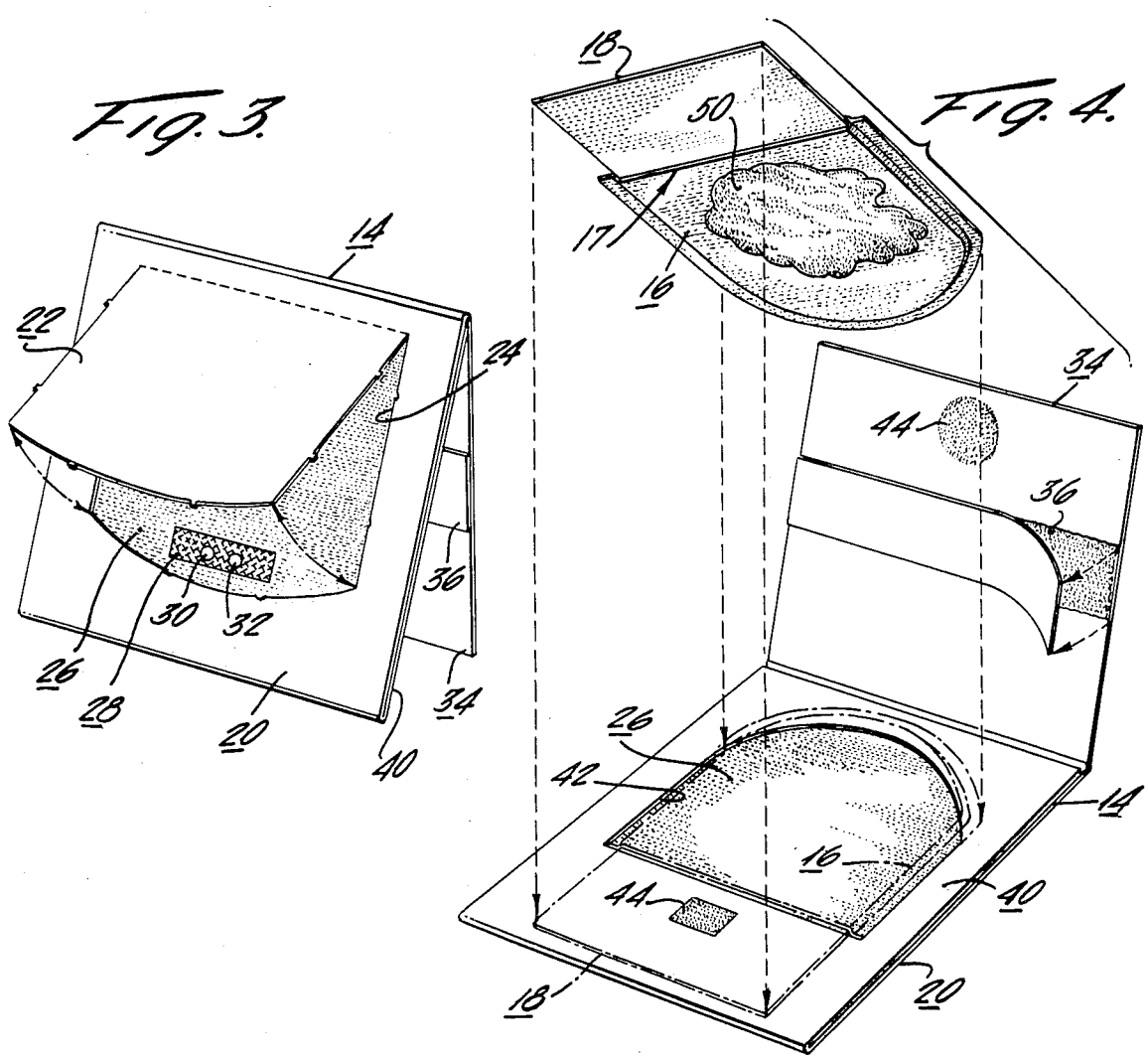

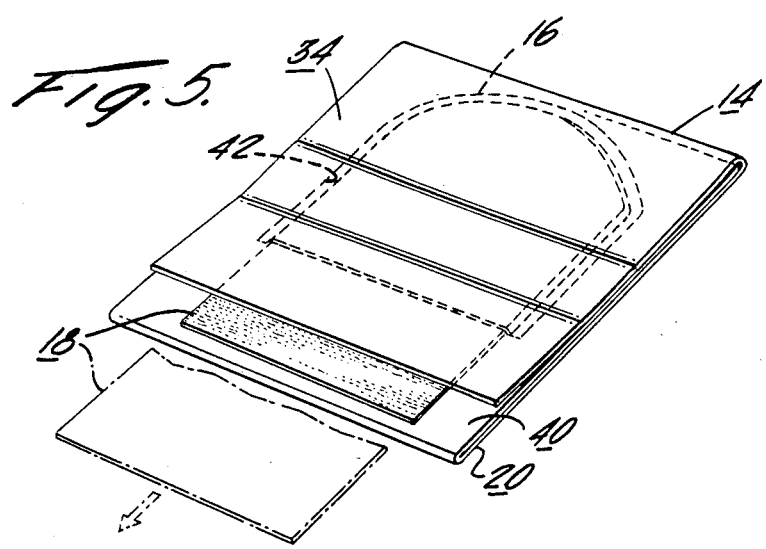
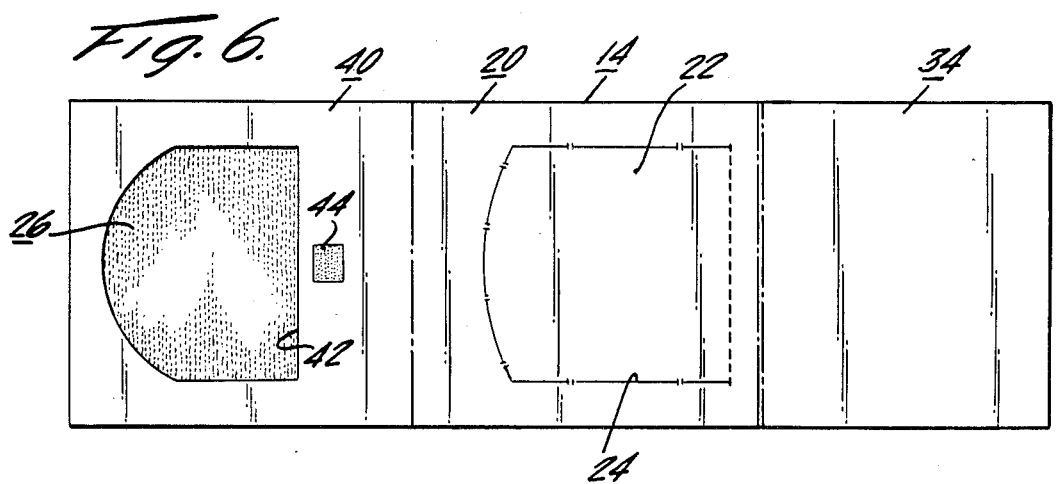
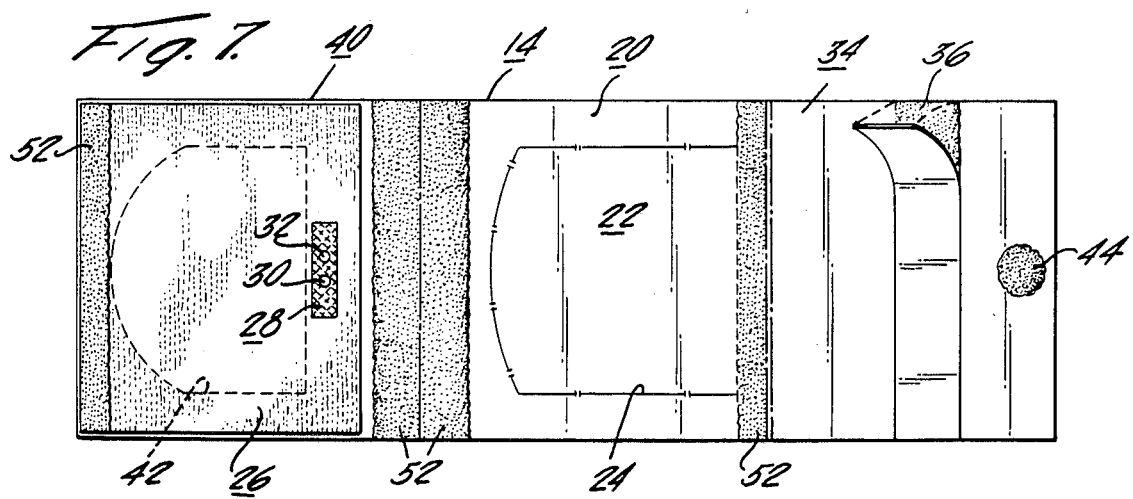

METHOD AND DEVICE FOR COLLECTING AND TESTING FOR FECAL OCCULT BLOOD

This invention relates to a convenient method and device for collecting and detecting occult blood in fecal matter. More particularly, this invention relates to a collection and test device that permits multiple analyses of a single fecal sample. The device of this invention can be used to collect, transport and carry out a variety of analyses in a single fecal sample at two different test sites of the device. The device can be employed in the privacy of one's home and is convenient and aesthetic to use.

Specimen slides and procedures for detecting occult blood in fecal matter are well known. Typically, in the case of a test for occult blood in feces, a sample of fecal matter is smeared on the specimen test sheet which has been treated with guaiac. A developing solution, such as a peroxide solution, is applied to the opposite side of the sheet. If blood is present in the fecal matter, the guaiac reaction will color the paper blue. This procedure is disclosed in U.S. Pat. No. 3,966,006.

One of the disadvantages associated with this test is that false positive results can occur, i.e., the positve result is not due to human hemoglobin. For example, non-hemoglobin interfering substances in the fecal matter such as peroxidases, various foodstuffs, drugs, and animal heme, which can be a result of meat in the diet, can give a positive result. A still further disadvantage is the inconvenience of obtaining a fecal sample from the toilet bowl.

Some of the above disadvantages may be minimized by the use of immunological tests which are specific for human hemoglobin. The enzyme immuno assay (EIA) for the detection of human hemoglobin in feces is known to the art. Briefly, the EIA test is a reaction between an antibody and an antigen (hemoglobin). The hemoglobin is reacted with a specific anti-human hemoglobin antibody and attached to the solid phase. This antibody-antigen complex is then reacted with anti-human hemoglobin which is conjugated to alkaline phosphatase. The enzymatic activity of the resulting complex bound to the solid phase is then quantified. A color intensity is measured instrumentally and the absorbance is directly related to the amount of human hemoglobin (antigen) in the sample. A typical EIA assay for fecal human hemoglobin is disclosed in U.S. Pat. No. 4,427,769.

However, the EIA assay described above also has its disadvantages. Human hemoglobin in fecal samples degrades with time. The degradation occurs with loss of antigenicity which results in falsely reduced values when employing the EIA assay. In brief, the immunoassay test specific for human hemoglobin requires that the hemoglobin retains its structural integrity. It has been discovered that guaiac is one component that has a deleterious effect on the stability of human hemoglobin.

A known device and method for conducting an immunoassay for fecal human hemoglobin is also disclosed in U.S. Pat. No. 4,427,769. In this device (Fecatest), the fluids from the fecal sample are passed through a guaiac impregnated filter paper onto an absorbent material before conducting an EIA assay. The following studies were conducted after storing fecal samples containing human hemoglobin in the Fecatest device.

Three fecal samples containing human blood were applied to and stored in the Fecatest device up to nine days and then analyzed by FECA-EIA Labsystems assay. The results, i.e., color intensity measured at an absorbance of 405 nm are set forth below in Table 1.

TABLE 1

| SAMPLE | R.T. STORAGE DURATION, DAYS | | | |
|---|---|---|---|---|
| No. | 0 | 1 | 3 | 9 |
| 1 | 2.05 | 0.48 | 0.13 * | 0.00 |
| 2 | 1.07 | 0.31 | 0.00 | 0.00 |
| 3 | 2.24 | 0.89 | 0.00 | 0.00 |

The above data clearly show the rapid degradation of hemoglobin with time. Virtually no color is seen on Day 3 on all samples.

When the same fecal samples were applied to the sampling device of the present invention and stored up to nine days, a surprising improvement in the stability of hemoglobin was observed. The EIA kit supplied by Labsystems as noted above was also employed to analyze these samples. The results are set forth in Table 2.

TABLE 2

| SAMPLE | R.T. STORAGE DURATION, DAYS | | | |
|---|---|---|---|---|
| No. | 0 | 1 | 3 | 9 |
| 1 | 2.62 | 1.71 | 1.56 | 0.86 |
| 2 | 2.36 | 2.58 | 1.10 | 0.26 |
| 3 | 2.06 | 1.40 | 0.96 | 0.32 |

Color is visible in all samples even after 9 days of storage at room temperature.

It is thus desirable that samples analyzed immunologically for human hemoglobin be protected from excessive contact with guaiac. The present invention minimizes guaiac contamination of the sample that may have to be analyzed immunologically for human hemoglobin.

It is therefore an object of this invention to provide a testing device and method which minimizes the guaiac contamination of the fecal sample that is to be analyzed immunologically for human hemoglobin.

It is a further object of this invention to provide a test device and method which permits the multiple analyses of a single fecal sample at two different test sites on the device.

It is an additional object of this invention to provide a test device and method for testing fecal occult blood which permits a convenient and aesthetic manner for collecting and transferring the fecal sample to the different test sites on the device.

Briefly, this invention consists of an improved test device for fecal occult blood which comprises two components. The first component is a fecal sampler employed to collect the fecal matter by direct wiping or patting of the anal area. The sampler is a combination of a pocket-like member and an absorbent insert which is retained within the pocket. The pocket is made of a soft paper having the consistency similar to toilet tissue and functions as a wipe pad.

The second component is a test slide having a guaiac treated specimen receiving sheet between a front panel and a rear panel with openings in each of the panels and pivotal covers to cover these openings, similar to the slide described in U.S. Pat. No. 3,996,006. This slide receives and retains the fecal sampler. The sampler is placed fecal smear side down in contact with the specimen receiving sheet. The sheet is bordered by a profiled aperture formed within the slide which resembles the wipe pad. The design is such that when the wipe pad is positioned within the aperture, and the front cover closed, a portion of the insert disposed in the wipe pad is exposed beyond the closure line of the cover. This enables one to withdraw the absorbent insert from the wipe pad pocket with the cover remaining closed. The insert which absorbs the fecal fluid from the wipe pad can be sectioned for a confirmatory assay such as an immunological assay. Thus, in one single collection and action, two separate membranes receive the fluids of the fecal sample and can be individually and independently tested. The guaiac sheet can be tested with a peroxide developing solution and the absorbent insert which is free of guaiac can be subjected to a confirmatory EIA assay.

A detailed description and better understanding of this invention can be had by referring to the accompanying drawings which show a preferred embodiment of the present invention.

FIG. 1 is a perspective view of a packaged test device of this invention;

FIG. 2 is a perspective view of the packaged testing device of FIG. 1 having been opened prior to use and showing the components of this invention contained therein;

FIG. 3 is an enlarged perspective view of the slide as viewed from the rear, showing rear flap opened exposing the testing surface incuding the control area;

FIG. 4 is a perspective view of the slide as viewed from the front in an opened mode about to receive a fecal sample to be tested;

FIG. 5 is a perspective view of the testing device in a closed mode prior to testing as viewed from the front;

FIGS. 6 and 7 are top and underside plan views respectively of blanks prior to folding, for preparing a slide in accordance with this invention;

Figure 8:
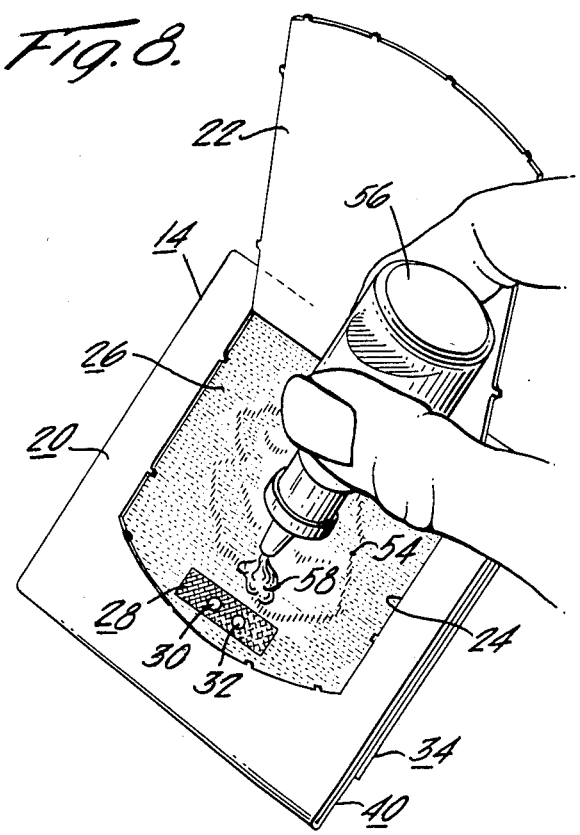
FIG. 8 is a perspective view of the rear panel of the slide showing a developing solution being applied to the testing surface including the control area.

Referring to FIG. 1 and FIG. 2, a pre-packaged testing device 10 has a tear off strip 12 on one edge of the package. The contents of the package test slide 14, wipe pad 16, and absorbent insert 18 are shown in FIG. 2. The testing area of the slide is revealed when flap 22 of rear panel 20 is opened. Between front panel 40 and the rear panel a specimen receiving sheet 26 is placed as viewed in insert 24. A portion of the sheet has a control area 28 which has a positive monitor 30 and a negative monitor 32. The appearance of the slide about to receive a fecal sample is shown in FIG. 4. It will be noted the front panel of the slide has a cover 34 which contains an adhesive strip 36 and a contact adhesive zone 44. The front panel has a profiled aperture 42 which resembles the design of wipe pad 16 and serves as a receptacle for the wipe pad which contains fecal sample 50. The wipe pad is a component of fecal sample 17 which also comprises the absorbent insert 18 contained within the wipe pad.

As illustrated in FIG. 5, after the fecal sample has been transferred to the slide and the front cover is closed, a portion of the insert is exposed beyond the closure line of the cover. It will be noted that the adhesive strip overlies the wipe pad and does not contact the insert. This permits the insert to be slidably withdrawn from the wipe pad with the cover maintained in a closed position.

To form the slide as shown in FIGS. 3 and 4, the panels of the blanks viewed in FIGS. 6 and 7 are folded and bonded together by adhesive bonds 52. These blanks comprise paper or cardboard.

Figure 9:
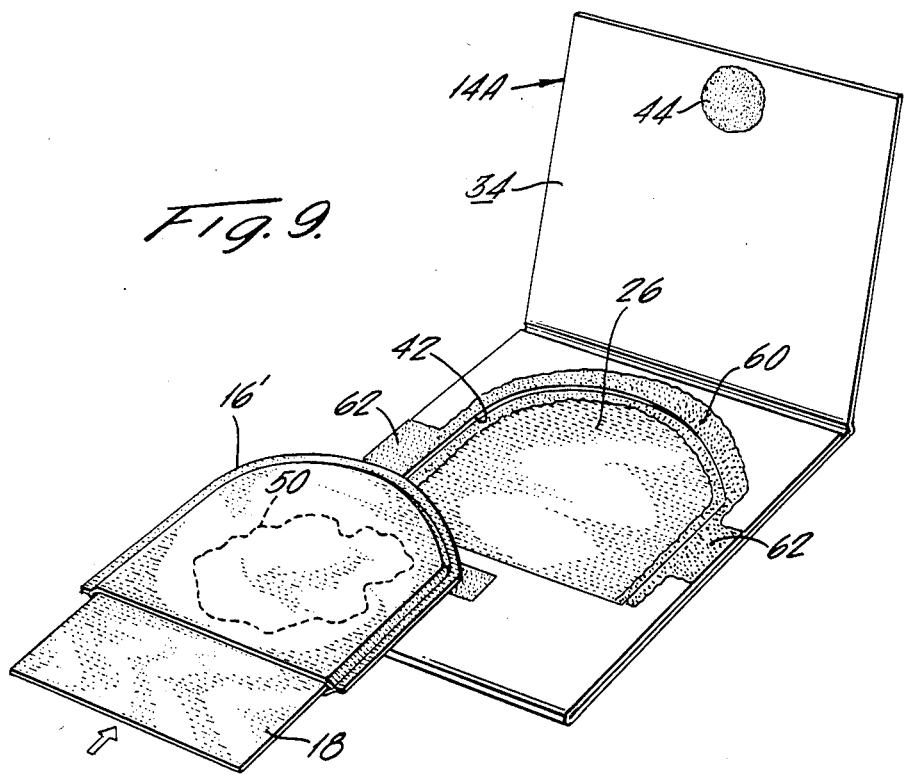
FIG. 9 is a perspective view of a modified slide demonstrating optional means to close the slide.
Figure 10:
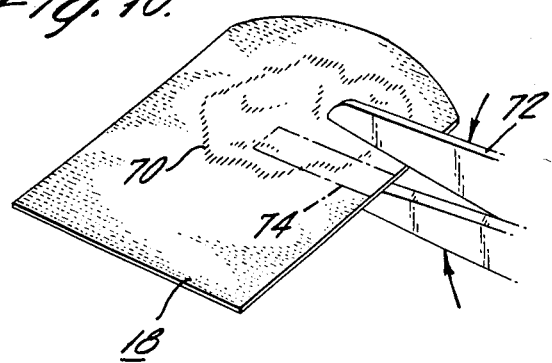
FIG. 10 is a perspective view of one form of the absorbent insert showing fecal stains and about to be cut in strips for additional testing.
Figure 11A:
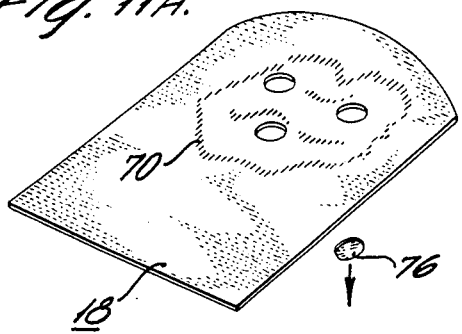
FIGS. 11A–11C are perspective views illustrating other embodiments for the absorbent insert.
Figure 11B:
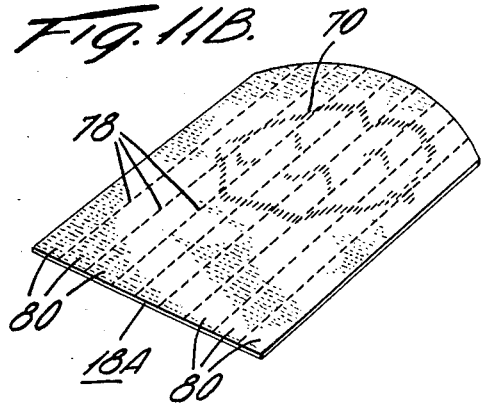
Figure 11C:
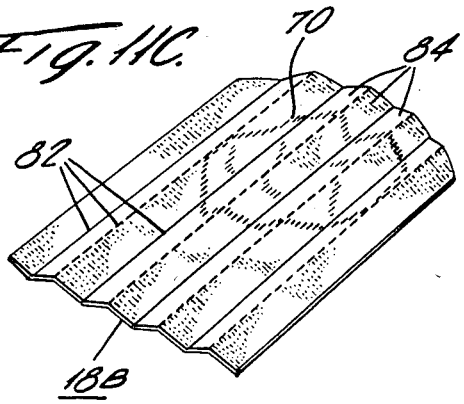

A modification of the slide 14A is shown in FIG. 9 wherein the profiled aperture 42 is bonded by a contact adhesive 60. The wipe pad in this case has a wider border 16' which enables the pad to contact adhesive 60 when transferred to the slide. In this manner the wipe pad is bonded to front panel 40 and the pad insert 18 is free to be slidably removed from the pad when the cover 34 is closed. Additional adhesive zones 62 centrally located on the sides of the front panel 40 permit a firm bonding the cover to the panel.

To use the slide, the patient separates cover 34 from panel 40. A fecal sample 50 is collected by direct wiping or patting of the anal area with the wipe pad portion 16 of sampler 17 after defecation. This is accomplished in the same manner as one would use toilet tissue. The fecal sampler with the smear side down is placed in contact with the specimen receiving sheet 26 which is bordered by a profiled aperture 42. The profile resembles the design of the wipe pad and serves as a receptacle for the pad. The peel off cover of adhesive strip 36 is removed and slide cover 34 is closed by bonding it to panel 40. The patient returns the slide either to his physician or a laboratory for analysis. The physician or technician removes absorbent insert 18 which was housed within wipe pad 16 as illustrated in FIG. 5. The insert is set aside while the guaiac test is developed. The physician or technician then pulls flap 22 free of panel 20 and opens it outwardly as viewed in FIG. 8. Through the opening thus made a developing solution 38, such as hydrogen peroxide, is applied to the receiving sheet 26 at stained area 54. The developing solution is also added to control area 28 to cover positive and negative monitors 30 and 32. The results are then observed, i.e., a blue color denotes a positive test.

Figure 12:
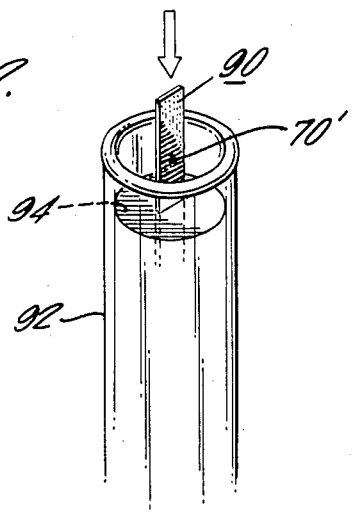
FIG. 12 is a perspective view illustrating a test strip obtained from the absorbent insert being placed in a tube containing reagents preparatory for EIA testing for human hemoglobin.

If the guaiac test is positive, the insert which was set aside is used to conduct a second confirmatory test, such as an immunological test specific for human hemoglobin. The insert, which is free of guaiac, can be cut into strips 70 or have discs 76 punched out. As noted in FIG. 12 a strip 90 can be placed in tube 92 containing reagent 94 to elute fecal matter 70' for an EIA assay.

The main advantage of this invention, therefore, is that in one single collection and action two separate membranes, i.e., the specimen receiving sheet and the absorbent insert, receive the components of the fecal sample and can be individually and independently tested. The fecal matter is placed in direct contact with the specimen receiving sheet which contains guaiac. The fluid from the fecal sample passes through the wipe pad and is collected on the insert which is free of guaiac. This design permits for both the standard test for fecal occult blood which depends on the hemoglobin catalyzed oxidation of guaiac and a confirmatory test such as an immunological assay specific for human hemoglobin in which the fecal sample should be relatively free of any contact with guaiac. Further, these tests can be conducted without disturbing or removing the fecal matter from the slide.

Another advantage of the device of this invention is that the construction is not air-tight and enough absorbent material is provided so that drying and aeration of the sample is facilitated. This is necessary to minimize microbial growth that may further degrade hemoglobin or other analytes of interest. Known sampling and testing devices that are kept tightly closed do promote growths of black and moldy spores.

A still further advantage of the sampling and testing device of this invention is that the test kit can include more than one fecal sampler per test. Any accidental loss of the wipe pad samples does not destroy the utility of the device. In the event that an adequate sample is not obtained in one wiping, one merely throws away the inexpensive wipe pad and tries another pad.

This invention also permits improved sample selection. The technician is presented with a relatively big absorbent insert containing the fecal components for an EIA assay. The technician is able to view the absorbent insert and punch out samples for EIA assay from areas of highest fecal concentration, i.e., the most stained areas. Such a selection is not possible with prior art devices where pre-cut discs absorb whatever amount of fecal fluid that comes through a guaiac containing membrane.

The above embodiments are illustrative and are not intended to be limiting.

What is claimed is:

1. A device for collecting and testing fecal occult blood comprising in combination:
    (a) a fecal sampler comprising a wipe pad and an insert retained therein;
    (b) a test slide comprising a front and rear panel, said front panel having means defining at least one aperture, said aperture being profiled to receive the wipe pad having a similar contour, sheet means carrying a test reagent between the front and rear panel for the reception of a fecal specimen, a hinged cover, having an open position and a closed position, to overlie a portion of the front panel and said aperture when in said closed position and flap means in the rear panel opposite said aperture and pivotable to expose the underside of the sheet, adhesive means positioned to contact and seal the wipe pad within said aperture when the cover is in said closed position whereby the insert which has a portion exposed beyond the closure line of the closed cover can be slidably removed from the sealed pad.

2. The device of claim 1 wherein the test reagent is guaiac.

3. The device of claim 1 wherein the adhesive means comprises a strip intermediate the hinged cover which contacts and seals the wipe pad when positioned within said aperture and when the cover is in said closed position.

4. The device of claim 1 wherein the adhesive means comprises contact adhesive means surrounding the profiled aperture which contacts and seals the wiping pad when the pad is placed in the aperture.

5. A method for determining the presence of fecal occult blood on a specimen test slide having a guaiac treated specimen receiving sheet between a front and rear panel with openings in the front and rear panels and pivotable covers to cover said openings which comprises:
    (a) obtaining a fecal specimen by direct wiping of the anal area with a fecal sampler which comprises a wipe pad and an insert;
    (b) transferring said specimen to the receiving sheet by placing the smear from the wipe pad in direct contact with the sheet;
    (c) closing the front cover of the test slide whereby the wipe pad is secured in the front opening and the insert has a portion exposed beyond the closure line;
    (d) removing the insert which contains fecal fluids which passed through the wipe pad from the feces;
    (e) opening the rear cover and applying a developing solution to the guaiac sheet at the corresponding opening in the rear panel, and if the test is positive,
    (f) conducting a second confirmatory test specific for human hemoglobin on said insert, said.sampler being free of guaiac.

6. A method for determining the presence of fecal occult blood on a specimen test slide having a guaiac treated specimen receiving sheet between a front and rear panel with openings in the front and rear panels and pivotable covers to cover said openings which comprises:
    (a) obtaining a fecal specimen by direct wiping of the anal area with a fecal sampler which comprises a wipe pad and an insert;
    (b) transferring said specimen to the receiving sheet by placing the smear from the wipe pad in direct contact with the sheet;
    (c) closing the front cover of the test slide whereby the wipe pad is secured in the front opening and the insert has a portion exposed beyond the closure line;
    (d) removing the insert which contains fecal fluids which passed through the wipe pad from the feces;
    (e) opening the rear cover and applying a developing solution to the guaiac sheet at the corresponding opening in the rear panel; and
    (f) conducting a second confirmatory test specific for human hemoglobin on said insert, said sampler being free of guaiac.

7. The method of claim 5 in which the second confirmatory test is an immunological assay.

8. A test kit for collecting and testing fecal occult blood which comprises:
    (a) the device of claim 1, and
    (b) a developing solution which reacts with said guaiac to color the sheet blue.

* * * * *